US008697728B2

(12) United States Patent
Ashrafian et al.

(10) Patent No.: US 8,697,728 B2
(45) Date of Patent: Apr. 15, 2014

(54) PERHEXILINE FOR USE IN THE TREATMENT OF HYPERTROPHIC CARDIOMYOPATHY (HCM)

(75) Inventors: Houman Ashrafian, London (GB); Michael Paul Frenneaux, Banchory (GB)

(73) Assignee: The University of Birmingham, Birmingham (GB)

( * ) Notice: Subject to any disclaimer, the term of this patent is extended or adjusted under 35 U.S.C. 154(b) by 9 days.

(21) Appl. No.: 13/319,986

(22) PCT Filed: May 11, 2010

(86) PCT No.: PCT/GB2010/050770
§ 371 (c)(1),
(2), (4) Date: Jan. 27, 2012

(87) PCT Pub. No.: WO2010/131033
PCT Pub. Date: Nov. 18, 2010

(65) Prior Publication Data
US 2012/0122925 A1    May 17, 2012

(30) Foreign Application Priority Data

May 13, 2009    (GB) .................................. 0908193.6

(51) Int. Cl.
*A61K 31/445*    (2006.01)
*C07D 417/00*    (2006.01)
(52) U.S. Cl.
USPC .......................................... 514/317; 546/192
(58) Field of Classification Search
USPC .......................................... 514/317; 546/192
See application file for complete search history.

(56) References Cited

U.S. PATENT DOCUMENTS

| 2003/0162824 A1 | 8/2003 | Krul |
| 2005/0203072 A1 | 9/2005 | Rudolph et al. |
| 2007/0275997 A1 | 11/2007 | Frenneaux |
| 2010/0331364 A1 | 12/2010 | Ashrafian et al. |
| 2012/0101128 A1 | 4/2012 | Frenneaux |

FOREIGN PATENT DOCUMENTS

| WO | 97/00678 | 1/1997 |
| WO | 2005/087233 | 9/2005 |
| WO | 2005/097121 | 10/2005 |
| WO | 2009/066085 | 5/2009 |
| WO | 2010/131033 | 11/2010 |
| WO | 2010/133815 | 11/2010 |

OTHER PUBLICATIONS

Lee et al. (European Heart Journal (2004) 25, 634-641.*
Lee et al. ((Circulation. 2005;112:3280-3288).*
Maron et al. Circulation. 2004; 109: 984-989.*
Lele et al (Circulation. 1995; 92: 2886-2894).*
Butera et al. (Heart 2003; 89; 205-206).*
Sasson et al. (JACC vol. 13(6) 1989 1275-1279.*
Abbate et al., "Recurrent angina after coronary revascularization: a clinical challenge." *Eur Heart J.*, 28:1057-65 (2007).
Abozguia et al., "Modification of myocardial substrate use as a therapy for heart failure." *Nat Clin Pract Cardiovasc Med.*; 3(9):490-498 (2006).
Abozguia et al., "The heart metabolism: Pathophysiological aspects in ischaemia and heart failiure.", *Curr Pharm Design*, 15:827-835 (2009).
Arany et al, "Transcriptional coactivator PGC-1α controls energy state and contractile function of cardiac muscle", *Cell Metabolism*, 1: 259-271 (2005).
Arany et al., "Transverse aortic constriction leads to accelerated heart failure in mice lacking PPAR-γ coactivator 1α ", *PNAS*, 103(26):10086-10091 (2006).
Ashrafian et al., "Metabolic mechanisms in heart failure", *Circulation*, 116:434-448 (2007).
Atherton et al., "Diastolic ventricular interaction in chronic heart failure", *Lancet*, 349:1720-1724 (1997).
Auricchio et al., "Clinical efficacy of cardiac resynchronization therapy using left ventricular pacing in heart failure patients stratified by severity of ventricular conduction delay", *J Am Coll Cardiol*, 42(12):2109-2116 (2003).
Bacharach et al., "Left ventricular peak ejection rate, filling rate and ejection fraction-frame requirements at rest and exercise: concise communication", *Journal of Nuclear Medicine*, 20:189-193 (1979).
Baicu et al, "Left ventricular systolic performance, function, and contractility in patients with diastolic heart failure", *Circulation*; 111:2306-2312 (2005).
Bhatia et al., "Outcome of heart failure with preserved ejection fraction in a population-based study",*N Engl J Med*, 355:260-269 (2006).
Boden et al., "Optimal medical therapy with or without PCI for stable coronary disease" *N Engl J Med*, 356(15):1503-1516 (2007).
Bonnefont et al., "Carnitine palmitoyltransferases 1 and 2: biochemical, molecular and medicinal aspects", *Mol Asp Med*, 25:495-520 (2004).
Borlaug et al., "Impaired chronotropic and vasodilator reserves limit exercise capacity in patients with heart failure and a preserved ejection fraction", *Circulation*, 114:2138-2147 (2006).
Brubaker et al., "Chronotropic incompetence and its contribution to exercise intolerance in older heart failure patients", *J Cardiopulm Rehabil*, 26:86-89 (2006).
Bruce RA, McDonough JR, "Stress testing in screening for cardiovascular disease", *Bull N Y Acad Med*, 5(12):1288-1305 (1969).
Buffon et al., "Widespread coronary inflammation in unstable angina" *N Engl J Med*, 347(1):5-12 (2002).

(Continued)

*Primary Examiner* — Shirley V Gembeh
(74) *Attorney, Agent, or Firm* — Nixon & Vanderhye P.C.

(57) ABSTRACT

The invention relates to perhexiline, or a pharmaceutically acceptable salt thereof, for use in the treatment of hypertrophic cardiomyopathy, as well as to a method of treating HCM, which comprises administering to an animal in need thereof an effective amount of perhexiline, or a pharmaceutically acceptable salt thereof, to treat said HCM. The invention further relates to a treatment programme for treating HCM, which involves the co-use or co-administration of perhexiline with one or more other compounds that are advantageous in treating HCM or the symptoms thereof.

18 Claims, 4 Drawing Sheets

(56) References Cited

OTHER PUBLICATIONS

Burkhoff et al., "Heart failure with a normal ejection fraction: is it really a disorder of diastolic function?", *Circulation*, 107:656-658 (2003).
Cavassila et al, "Cramer-Rao bounds: an evaluation tool for quantitation", *NMR Biomed*, 14:278-283 (2001).
Chatterjee et al., "Systolic and Diastolic Heart Failure: Differences and Similarities", *Journal of Cardiac Failure*, 13(7):569-576 (2007).
Chen et al., "Noninvasive single-beat determination of left ventricular end-systolic elastance in humans", *J Am Coll Cardiol*, 38:2028-2034 (2001).
Chirkov, YY, Horowitz JD, "Impaired tissue responsiveness to organic nitrates and nitric oxide: a new therapeutic fronteer?", *Pharmacology & Therapeutics*, 116:287-305 (2007).
Cicoira et al., "Long-term, dose-dependent effects of spironolactone on left ventricular function and exercise tolerance in patients with chronic heart failure", *J Am Coll Cardiol*, 40(2):304-310 (2002).
Coats et al., "Current management of 1-8 hypertrophic cardiomyopathy", *Current Treatment Options in Cardiovascular Medicine*, 10:496-504 (2008).
Cohn, J., "The Management of Chronic Heart Failure", *New England Journal of Medicine*, 335(7):490-498(1996).
Cole et al., "Efficacy and safety of perhexiline maleate in refractory angina. A double-blind placebo-controlled clinical trial of a novel antianginal agent", *Circulation*, 81:1260-1270 (1990).
Cooper et al., "Studies on the metabolism of perhexiline in man", *Eur J Clin Pharmacol*, 32:569-576 (1987).
Cooper et al., "Polymorphic hydroxylation of perhexiline maleate in man", *J Med Genetics*, 21:27-33 (1984).
Czerwinski et al. "A controlled study of the diuretic and natriuretic of perhexiline maleate in normal human volunteers", *Postgraduate Medical Journal*, (April Suppl.): 26-31 (1973).
Davies et al., "CYP2B6, CYP2D6, and CYP3A4 catalyze the primary oxidative metabolism of perhexiline enantiomers by human liver microsomes", *Drug Metab Dispos*, 35(1):128-138 (2007).
Davies et al, "Determination of the 4-monohydroxy metabolites of perhexiline in human plasma, urine and liver microsomes by liquid chromatography," *Journal of Chromatography B*, 843:302-309 (2006).
Davies et al., "Enantioselective assay for the determination of perhexiline enantiomers in human plasma by liquid chromatography", *Journal of Chromatography B*, 832: 114-120 (2006).
Davies et al., "Steady-state pharmacokinetics of the enantiomers of perhexiline in CYP2D6 poor and extensive metabolizers administered rac-perhexiline," *Br J Clin Pharmacol*, 65(3):347-354 (2008).
Davies NJ and Denison DM, "The measurement of metabolic gas exchange and minute volume by mass spectrometry alone", *Respiration Physiology*, 36(2):261-267 (1979).
Depre et al., "Glucose for the Heart", *Circulation*, 99:578-588 (1999).
Deschamps et al., "Inhibition by perhexiline of oxidative phosphorylation and the β-oxidation of fatty acids: possible role in pseudoalcoholic liver lesions", *Hepatology*, 19: 948-61 (1994).
Eckberg et al., "Defective cardiac parasympathetic control in patients with heart disease", *N Engl J Med*, 285(16):877-883 (1971).
Fardeau et al., "Muscle and nerve changes induced by perhexiline maleate in man and mice", *Muscle & Nerve*, 2:24-36 (1979).
Folmes et al., "High rates of residual fatty acid oxidation during mild ischaemia decrease cardiac work and efficiency", *J Mol Cell Cardiol*, 47:142-148 (2009).
Fragasso et al., "Effects of metabolic modulation by trimetazidine on left ventricular function and phosphocreatine/adenosine triphosphate ratio in patients with heart failure", *Eur Heart J*, 27:942-948 (2006).
Frenneaux, M, "New tricks for an old drug", *European Heart Journal*, 23:1898-1899 (2002).
Fromenty B, Pessayere D, "Inhibition of mitochondrial beta-oxidation as a mechanism of hepatotoxicity", *Pharmac Ther*; 67(1):101-154 (1995).
Fukuda et al., "Phosphorylation of Titin Modulates Passive Stiffness of Cardiac Muscle in a Titin Isoform-dependent manner",*J Gen Physiol*, 125:257-271 (2005).
Furst W and Hallstrom S, "Simultaneous determination of myocardial nucleotides, nucleosides, purine bases and creatine phosphate by ion-pair high-performance liquid chromatography", *J Chromatogr B*, 578: 39-44 (1992).
Gillebert et al., "Relaxation-systolic pressure relation: A load-independent assessment of left ventricular contractility", *Circulation*, 95:745-752 (1997).
Grossman et al., "Contractile state of the left ventricle in man as evaluated from end-systolic pressure-volume relations", *Circulation*, 56:845-852 (1977).
Heusch G., "Hibernating myocardium", *Physiol Rev*, 78(4):1055-1085 (1998).
Higginbotham et al., "Regulation of stroke volume during submaximal and maximal upright exercise in normal man", *Circ Res*, 58:281-291 (1986).
Holden K R, "Chronic Heart Failure and Disability" [Online] Aug. 7, 2007, *Disability Doc-Examining Social Security Disability*, Retrieved from the Internet: URL:http://www.disabilitydoc.com/chronic-heart~failure-and-disa/> (2007).
Horowitz et al., "Perhexiline maleate treatment for severe angina pectoris—correlations with pharmacokinetics", *Int J Cardiol*, 13:219-229 (1986).
Hulsmann et al., "Long-term effect of atenolol on ejection fraction, symptoms, and exercise variables in patients with advanced left ventricular dysfunction", *J Heart Lung Transplant*, 20:1174-1180 (2001).
Hunt et al., "ACC/AHA 2005 Guideline Update for the Diagnosis and Management of Chronic Heart Failure in the Adult: a report of the American College of Cardiology/American Heart Association Task Force on Practice Guidelines (Writing Committee to Update the 2001 Guidelines for the Evaluation and Management of Heart Failure): developed in collaboration with the American College of Chest Physicians and the International Society for Heart and Lung Transplantation: endorsed by the Heart Rhythm Society", *Circulation*, 112:e154-e235 available at www.acc.org (2005).
Inglis et al., "Effect of CYP2D6 metabolizer status on the disposition of the (+) and (−) enantiomers of perhexiline in patients with myocardial ischaemia", *Pharmacogenetics Genomics*, 17:305-312 (2007).
Ingwall JS and Weiss RG, "Is the failing heart energy starved?: On using chemical energy to support cardiac function", *Circulation Research*, 95:135-145 (2004).
Irvine et al., "Nitroxyl (HNO): the Cinderella of the nitric oxide story", *Trends in Pharmacol Sci*, 29(12):601-608 (2008).
Jeffrey et al, "Direct evidence that perhexiline modifies myocardial substrate utilization from fatty acids to lactate", *J Cardiovasc Pharmacol*, 25:469-472 (1995).
Kannel WB, "Incidence and epidemiology of heart failure", *Heart Failure Rev*, 5:167-173 (2000).
Kawaguchi et al., "Combined ventricular systolic and arterial stiffening in patients with heart failure and preserved ejection fraction: implications for systolic and diastolic reserve limitations", *Circulation*, 107:714-720 (2003).
Kennedy et al., "Effect of the anti-anginal agent, perhexiline, on neutrophil, valvular and vascular superoxide formation", *Eur J Pharmacol*, 531:13-19 (2006).
Kennedy et al., "Inhibition of carnitine palmitoyltransferase-1 in rat heart and liver by perhexiline and amiodarone", *Biochem Pharmacol*, 52:273-280 (1996).
Kennedy et al., "Effect of perhexiline and oxfenicine on myocardial function and metabolism during low-flow ischemia/reperfusion in the isolated rat heart", *J Cardiovasc Pharmacol*, 36(6):794-801 (2000).
Killalea SM and Krum H, "Systematic review of the efficacy and safety of perhexiline in the treatment of ischemic heart disease", *Am J Cardiovasc Drugs*, 1(3):193-204 (2001).
Kiriazis H and Kranias EG, "Genetically engineered models with alterations in cardiac membrane calcium-handling proteins", *Annu Rev Physiol*, 62:321-351 (2000).

(56) References Cited

OTHER PUBLICATIONS

Kitakaze, Masashi et al., "New role of adenosine for the treatment of ischemic heart disease", *Journal of Clinical and Experimental Medicine* (IGAKU NO AYUMI), 192(1):35-39 (2000).
Lamb et al., "Diastolic dysfunction in hypertensive heart disease is associated with altered myocardial metabolism", *Circulation*, 99:2261-2267. (1999).
Lang et al., "Recommendations for chamber quantification: a report from the American Society of Echocardiography's Guidelines and Standards Committee and the Chamber Quantification Writing Group, developed in conjunction with the European Association of Echocardiography, a branch of the European Society of Cardiology", *J Am Soc Echocardiogr*, 18:1440-1463 (2005).
Lee et al., "Metabolic manipulation of ischaemic heart disease, a novel approach to treatment", *Eur Heart J*, 25:634-641 (2004).
Lee et al., "Augmentation of Glucose Metabolism With Perhexiline Improves Maximal Oxygen Consumption and Quality of Life in Patients With Nonischaemic Dilated Cardiomyopathy", *Journal of the American College of Cardiology*, 43(5): 190-A-1088-122(2004).
Lee et al., "Metabolic modulation with perhexiline in chronic heart failure: a randomized, controlled trial of short-term use of a novel treatment", *Circulation*, 112:3280-3288 (2005).
Leite-Moreira et al., "Afterload induced changes in myocardial relaxation: a mechanism for diastolic dysfunction", *Cardiovasc Res*, 43:344-353 (1999).
Lele et al., "Determinants of exercise capacity in patients with coronary artery disease and mild to moderate systolic dysfunction. Role of heart rate and diastolic filling abnormalities", *Eur Heart J*, 17(2):204-212 (1996).
Lele et al., "Exercise capacity in hypertrophic cardiomyopathy. Role of stroke volume limitation, heart rate, and diastolic filling characteristics", *Circulation*, 92:2886-2894 (1995).
Liberts et al., "Effects of perhexiline and nitroglycerin on vascular, neutrophil and platelet function in patients with stable angina pectoris", *Eur J Pharmacol*, 560: 49-55 (2007).
Lindahl et al., "Markers of myocardial damage and inflammation in relation to long-term mortality in unstable coronary artery disease", *N Engl J Med*, 343: 1139-1147 (2000).
Lopaschuk et al., "An imbalance between glycolysis and glucose oxidation is a possible explanation for the detrimental effects of high levels of fatty acids during aerobic reperfusion of ischemic hearts", *J Pharmacol Exp Ther*, 264(1):135-144 (1993).
Magorien et al., "Hemodynamic correlates for timing intervals, ejection rate and filling rate derived from the radionuclide angiographic volume curve", *Am J Cardiol*, 53:567-571 (1984).
Mann, DL, "Mechanisms and Models in Heart Failure: A Combinatorial Approach", *Circulation*, 100:999-1008 (1999).
Mannheimer et al., "The problem of chronicrefractory angina", *Eur Heart J*, 23: 355-370 (2002).
Mantero et al., "Left ventricular diastolic parameters in 288 normal subjects from 20 to 80 years old", *Eur Heart J*, 16:94-105 (1995).
Metra et al., "Treatment of advanced chronic heart failure with normal left ventricular ejection fraction. Response to the letter by Dr. Martinez-Selles", *European Journal of Heart Failure*, 9(12)1224-1225 (2007).
Metra et al., "Advanced chronic heart failure: A position statement from the Study Group on Advanced Heart Failure of the Heart Failure Association of the European Society of Cardiology", *European Journal of Heart Failure*, 9:684-694 (2007).
Morgan et al., "Impaired oxidation of debrisoquine in patients with perhexiline liver injury", *Gut*, 25: 1057-1064 (1984).
Murnaghan MF, "Effect of fatty acids on the ventricular arrhythmia threshold in the isolated heart of the rabbit", *Br J Pharmacol*, 73(4):909-915 (1981).
Najjar et al., "Age and gender affect ventricular-vascular coupling during aerobic exercise", *J Am Coll Cardiol*, 44:611-617 (2004).
Naressi et al., "Java-based graphical user interface for MRUI, a software package for quantitation of in vivo/medical magnetic resonance spectroscopy signals", *Comput Biol Med*, 31(4):269-286 (2001).

Neubauer et al., "Myocardial phosphocreatine-to-ATP ratio is a predictor of mortality in patients with dilated cardiomyopathy", *Circulation*, 96:2190-2196 (1997).
Neubauer et al., "Contributions of 31P-magnetic resonance spectroscopy to the understanding of dilated heart muscle disease", *Eur Heart J*, 16(Suppl O):115-118 (1995).
Neubauer et al., "31P magnetic resonance spectroscopy in dilated cardiomyopathy and coronary artery disease. Altered cardiac high-energy phosphate metabolism in heart failure", *Circulation*, 86(6):1810-1818 (1992).
Neubauer S, "The failing heart—an engine out of fuel", *N Engl J Med*, 356: 1140-1151 (2007).
Nihoyannopoulos et al., "Diastolic function in hypertrophic cardiomyopathy: relation to exercise capacity", *J Am Coll Cardiol*, 19:536-540 (1992).
O'Brien et al., "Cardiac troponin I is a sensitive, specific biomarker of cardiac injury in laboratory animals", *Laboratory Animals*; 40:153-171 (2006).
Ommen et al., "Clinical utility of Doppler echocardiography and tissue Doppler imaging in the estimation of left ventricular filling pressures: A comparative simultaneous Dopplercatheterization study", *Circulation*, 102:1788-1794 (2000).
Ordidge et al, "Separate water and fat MR images", Letters to the Editor, *Radiology*, 157(2):551-553 (1985).
Peltier et al., "Treatment practices in heart failure with preserved left ventricular ejection fraction: A prospective observational study", *International Journal of Cardiology*, 118(3):363-369 (2007).
Pena JR and Wolska BM, "Troponin I phosphorylation plays an important role in the relaxant effect of β-adrengergic stimulation in mouse hearts", *Cardiovasc Res*, 61:756-763 (2004).
Pepine et al., "Alteration of left ventricular responses to ischemia with oral perhexiline", *Postgraduate Medical Journal*, April Suppl:43-46 (1973).
Pepine et al., "Effects of perhexiline on coronary hemodynamic and myocardial metabolic responses to tachycardia", *Circulation*, 49:887-893 (1974).
Perseghin et al., "Left ventricular function and energy metabolism in middle-aged men undergoing long lasting sustained aerobic oxidative training", *Heart Online* (downloaded from heart.bmj.com-Nov. 21, 2008) doi:10.1136/hrt.2008.154716 (published online Nov. 13, 2008).
Phan et al., "Dynamic changes in left ventricular function on exercise in heart failure with preserved ejection fraction: the role of myocardial energy deficiency", *Heart*, 95:114 (2009).
Phan et al., "Heart Failure With Preserved Ejection Fraction Is Characterized by Dynamic Impairment of Active Relaxation and Contraction of the Left Ventricle on Exercise and Associated With Myocardial Energy Deficiency", *J. Am. Coll. Cardiol.*, 54:402-409 (2009).
Porrello et al, "Heritable pathologic cardiac hypertrophy in adulthood is preceded by neonatal cardiac growth restriction", *Am J Physiol Regul Integr Comp Physiol*, 296:R672-R680 (2009).
Poupon et al., "Perhexiline maleate-associated hepatic injury prevalence and characteristics", *Digestion*, 20: 145-150 (1980).
Ritchie et al., "Exploiting cGMP-based therapies for the prevention of left ventricular hypertrophy: NO & beyond", *Pharmacol Ther*, 124:279-300 (2009).
Ritchie et al., "B-type Natriuretic Peptide: Endogenous regulator of myocardial structure, biomarker and therapeutic target", *Curr Mol Med*, 9:814-25 (2009).
Robertson et al., "The effect of troponin I phosphorylation on the $Ca^{2+}$-binding properties of the $Ca^{2+}$-regulatory site of bovine cardiac troponin", *J Biol Chem*, 257(1):260- 263 (1982).
Rossi et al., "Chronic heart failure with preserved left ventricular ejection fraction: Diagnostic and prognostic value of left atrial size", *International Journal of Cardiology*, 110(3):386-392 (2006).
Rupp et al, "The use of partial fatty acid oxidation inhibitors for metabolic therapy of angina pectoris and heart failure", *Herz*, 27:621-636 (2002).
Sallustio et al., "Pharmacokinetics of the antianginal agent perhexiline: relationship between metabolic ratio and steady-state dose", *Br J Clin Pharmacol*, 54:107-14 (2002).

(56) References Cited

OTHER PUBLICATIONS

Scheuermann-Freestone et al., "Abnormal cardiac muscle function in heart failure is related to insulin resistance", *Cardiovasc J S Afr*, 15(4 Suppl 1):12, #52 (2004).
Scheuermann-Freestone et al., "Abnormal cardiac and skeletal muscle energy metabolism in patients with type 2 diabetes", *Circulation*, 107:3040-3046 (2003).
Seth et al., "Alterations in isoproterenol-induced cardiac metabolic changes by perhexiline", *Indian J Med Res*, 81:224-229 (1985).
Shinke, Toshirou, "Treatment of Heart Failure Associated With Ischemic Heart Disease", *Clinical Practice and Study*, 78(9):73-79 (2001).
Shivu et al., "31P magnetic resonance spectroscopy to measure in vivo cardiac energetics in normal myocardium and hypertrophic cardiomyopathy: Experiences at 3T", *Eur J Radiol*, 73:255-259 (2010).
Singlas et al., "Pharmacokinetics of perhexiline maleate in anginal patients with and without peripheral neuropathy", *Eur J Clin Pharmacol*, 14:195-201 (1978).
Smith et al., "Altered creatine kinase adenosine triphosphate kinetics in failing hypertrophied human myocardium", *Circulation*, 114:1151-1158 (2006).
Stanley et al., "Myocardial substrate metabolism in the normal and failing heart", *Physiol Rev*, 85:1093-129 (2005).
Stewart et al., "More 'malignant' than cancer? Five-year survival following a first admission for heart failure", *Eur J Heart Fail*, 3:315-322 (2001).
Stewart et al., "Relationship between plasma perhexiline concentration and symptomatic status during short-term perhexiline therapy", *Ther Drug Monit*, 18:635-639 (1996).
Szibor M and Holtz J, "Mitochondrial ageing", *Basic Res Cardiol*, 98:210-218 (2003).
Takei, Kumiko et al., "Three Cases of Acute Exacerbation of Chronic Heart Failure Treated With Milrinone", *Therapeutic Research*, 20(8):245-251 (1999).
Takimoto et al., "Frequency-and afterload-dependent cardiac modulation in vivo by troponin I with constitutively active protein kinase a phosphorylation sites", *Circ Res*, 94:496-504 (2004).
Teerlink et al., "Progressive ventricular remodeling in response to diffuse isoproterenol-induced myocardial necrosis in rats", *Circ Res*, 75:105-113 (1994).
Teo et al., "Perhexiline during exercise training in coronary heart disease", *Clinical Pharmacology and Therapeutics*, 34(6):744-748 (1983).
Unger et al., "Dissociation between metabolic and efficiency effects of perhexiline in normoxic rat myocardium", *J Cardiovasc Pharmacol*, 46:849-855 (2005).
Unger et al., "Perhexiline improves symptomatic status in elderly patients with severe aortic stenosis", *Aust NZ J Med*, 27:24-28 (1997).
Vasan et al., "Prevalence, clinical features and prognosis of diastolic heart failure: an epidemiologic perspective", *JACC*, 26(7):1565-1574 (1995).
Vescovo et al., "Improved exercise tolerance after losartan and enalapril in heart failure: correlation with changes in skeletal muscle myosin heavy chain composition", *Circulation*, 98(17):1742-1749 (1998).

Westermann et al., "Role of left ventricular stiffness in heart failure with normal ejection fraction", *Circulation*, 117:2051-2060 (2008).
Willoughby et al., "Beneficial clinical effects of perhexiline in patients with stable angina pectoris and acute coronary syndromes are associated with potentiation of platelet responsiveness to nitric oxide", *Eur Heart J*, 23:1946-1954 (2002).
Willoughby et al., "Platelet nitric oxide responsiveness: a novel prognostic marker in acute coronary syndromes", *Arterioscler Thromb Vasc Biol*, 25: 2661-2666 (2005).
Wright et al., "The absorption, excretion and metabolism of perhexiline maleate by the human", *Postgrad Med J*, 49 (April Suppl 3):8-15 (1973).
Yagi et al., "Sustained currents through ASIC3 ion channels at the modest pH changes that occur during myocardial ischemia", *Circ Res*, 99:501-509 (2006).
Yang et al., "Current and future treatment strategies for refractory angina", *Mayo Clin Proc*, 79(10):1284-1292 (2004).
Yu et al., "Progression of systolic abnormalities in patients with "isolated" diastolic heart failure and diastolic dysfunction", *Circulation*, 105:1195-1201 (2002).
Zanger et al., "Cytochrome P450 2D6: overview and update on pharmacology, genetics and biochemistry", *Naunyn-Schmiedeberg's Arch Pharmacol*, 369:23-37 (2004).
Zhang et al, "Cardiac troponin I phosphorylation increases the rate of cardiac muscle relaxation", *Circ Res*, 76:1028-1035.
Zile et al., "Diastolic heart failure—abnormalities in active relaxation and passive stiffness of the left ventricle", *N Engl J Med*, 350:1953-1959 (2004).
Zile MR and Brutsaert DL, "New concepts in diastolic dysfunction and diastolic heart failure: Part I: diagnosis, prognosis, and measurements of diastolic function", *Circulation*, 105:1387-1393 (2002).
Notification of Reasons for Refusal issued in JP 2007-502376, (with English translation) Jan. 12, 2011.
Hunt et al., "ACC/AHA Guidelines for the Evaluation and Management of Chronic Heart Failure in the Adult: Executive Summary a Report of the American College of Cardiology/American Heart Association Task Force on Practice Guidelines (Committee to Revise the 1995 Guidelines for the Evaluation and Management of Heart Failure)" *Circulation*, 104:2996-3007 (2001).
Ashrafian et al., "Perhexiline," *Cardiovascular Drug Reviews*, 25(2):76-97 (2007).
Williams et al., "Syncope in hypertrophic cardiomyopathy: mechanisms and consequences for treatment," *Europace*, 9:817-822 (2007).
Gould et al., "Stereoselective pharmacokinetics of perhexiline," *Xenobiotica*, 16(5):491-502 (1986).
Drexler et al., "Explaining Fatigue in Congestive Heart Failure," *Annu. Rev. Med.*, 47:241-256 (1996).
Jerant et al., "Reducing the Cost of Frequent Hospital Admissions for Congestive Heart Failure: A Randomized Trial of a Home Telecare Intervention," *Medical Care*, 39(11):1234-1245 (2001).
Krum, "Guidelines for management of patients with chronic heart failure in Australia," *The Medical Journal of Australia*, 174(9):459-466 (2001).
De Keulenaer et al., "Systolic and diastolic heart failure: Different phenotypes of the same disease?" *European Journal of Heart Failure*, 9:136-143 (2007).

* cited by examiner

PERHEXILINE FOR USE IN THE TREATMENT OF HYPERTROPHIC CARDIOMYOPATHY (HCM)

CROSS-REFERENCE TO RELATED APPLICATIONS

This application is the National Stage of International Application No. PCT/GB2010/050770, filed May 11, 2010, which claims the benefit of GB 0908193.6, filed May 13, 2009, the entire contents of which are incorporated by reference herein.

FIELD OF THE INVENTION

The invention relates to treatment of hypertrophic cardiomyopathy (HCM) in animal subjects, in particular humans.

BACKGROUND OF THE INVENTION

Hypertrophic cardiomyopathy, characterised by unexplained cardiac hypertrophy, is the commonest inherited cardiac condition (prevalence ~0.2%). The clinical manifestations of HCM can range from the complete absence of symptoms to dyspnoea, chest pains, palpitations, and syncope; HCM's first presentation may even be as sudden cardiac death. Left ventricular outflow tract obstruction that accounts for some of these symptoms in a proportion of HCM patients, may be amenable to drug therapies and to interventions such as surgical septal myectomy or alcohol septal ablation. However, less progress has been made, in the treatment of the substantial number of patients with HCM without obstruction, in whom dyspnoea appears to be primarily due to diastolic dysfunction. Evidence supporting the benefit of the negative chrono-inotropes (eg, beta-blockers, verapamil, disopyramide), which are extensively used by these patients, is limited mandating a better understanding of the mechanisms underlying HCM with the intention of identifying novel therapies.

HCM is a disease of the perturbed sarcomere, with >400 mutations having been identified in genes encoding cardiac contractile proteins (e.g. β-myosin heavy chain, cardiac myosin-binding protein-C, α-tropomyosin, cardiac troponin T and I). HCM-causing mutations increase sarcomeric $Ca^{2+}$ sensitivity, ATPase activity and the energetic "tension cost" of myocyte contraction. These biophysical considerations have led to the proposal that the pathophysiology of HCM is attributable, at least in part, to excessive sarcomeric energy use. Supporting this proposal, myocardial energy defects have been associated with HCM, in both animal and human disease. Indeed, consistent with a functional role for this energy deficiency, LV relaxation (an energy requiring process), has been observed to be aberrant in HCM.

Perhexiline (2-(2,2-dicyclohexylethyl) piperidine) is a known anti-anginal agent that operates principally by virtue of its ability to shift metabolism in the heart from free fatty acid metabolism to glucose, which is more energy efficient.

WO-A-2005/087233 discloses the use of perhexiline for the treatment of chronic heart failure (CHF) where the CHF is a result of an initial inciting influence of ischaemia or where the CHF is a result of an initial non-ischaemic inciting influence.

SUMMARY OF THE INVENTION

According to a first aspect of the present invention, there is provided a method of treating hypertrophic cardiomyopathy (HCM), which comprises administering to an animal in need thereof an effective amount of perhexiline, or a pharmaceutically acceptable salt thereof, to treat said HCM. The animal is preferably a mammal and most preferably a human.

The HCM treated may be obstructive HCM or non-obstructive HCM.

According to another aspect of the present invention, perhexiline, or a pharmaceutically acceptable salt thereof, is provided for use in the treatment of HCM.

According to a further aspect of the invention there is provided a treatment programme for treating HCM, which involves the co-use or co-administration of perhexiline or pharmaceutically acceptable salt thereof with one or more other compounds that are advantageous in treating HCM or the symptoms thereof, for example a calcium channel blocker such as verapamil, or a beta blocker.

BRIEF DESCRIPTION OF THE DRAWINGS

FIG. 2A represents the peak oxygen consumption (peak $V_{O2}$) results;

FIG. 2B represents the diastolic ventricular filling results (nTTPF, normalized for heart rate Time To Peak Filling) and shows that PCr/ATP ratio (a measure of cardiac energetic state) is lower in HCM patients versus controls;

FIG. 2C is an example of $^{31}P$ cardiac spectra of a HCM patient in which Point C indicates centre of phosphorus coil, VOI; voxel of interest, 2,3-DPG indicates 2,3-diphosphoglycerate; PDE, phosphodiesters; PCr, phosphocreatine; α, β, γ indicate the three phosphorus nuclei of ATP, and shows that nTTPF (a measure of the rate of active relaxation of the LV) is essentially unchanged on exercise in the controls bu abnormally slows in the HCM patients; and FIG. 2D represent the myocardial energetic results (PCr/γ ATP ratio) and shows that exercise capacity (peak VO2) is lower in HCM patients versus controls.

DETAILED DESCRIPTION OF THE INVENTION

In aspects of the present invention, the perhexiline exists in the form of a salt of perhexiline, preferably the maleate salt.

The perhexiline may be used at doses titrated to achieve therapeutic but non-toxic plasma perhexiline levels (Kennedy J A, Kiosoglous A J, Murphy G A, Pelle M A, Horowitz J D. "Effect of perhexiline and oxfenicine on myocardial function and metabolism during low-flow ischemia/reperfusion in the isolated rat heart", J Cardiovasc Pharmacol 2000; 36(6):794-801). Typical doses for a normal patient would be 100 mg to 300 mg daily, although smaller doses may be appropriate for patients who are slow metabolisers of perhexiline.

Physiologically acceptable formulations, such as salts, of the compound perhexiline, may be used in the invention. Additionally, a medicament may be formulated for administration in any convenient way and the invention therefore also includes within its scope use of the medicament in a conventional manner in a mixture with one or more physiologically acceptable carriers or excipients. Preferably, the carriers should be "acceptable" in the sense of being compatible with the other ingredients of the formulation and not deleterious to the recipient thereof. The medicament may be formulated for oral, buccal, parental, intravenous or rectal administration. Additionally, or alternatively, the medicament may be formulated in a more conventional form such as a tablet, capsule, syrup, elixir or any other known oral dosage form.

Perhexiline exists as two enantiomers, (+)-perhexiline and (−)-perhexiline which are known to be metabolized differently based on patient genotype. It has further been proposed that the atypical kinetics observed in the inhibition of both cardiac and liver derived CPT-1 may have been due to different inhibition affinities of each enantiomer of perhexiline for both the muscle and liver isoforms of CPT-1, and that (+)- and (−)-perhexiline may exhibit differential selectivity for target enzymes in cardiac and hepatic tissues.

In accordance with the invention, perhexiline may be used as a racemic mixture (typically a 50:50 mixture of the enantiomers), or as one or other of the (+)-perhexiline and (−)-perhexiline enantiomers, or as a mixture of the two enantiomers in any ratio.

Based on relative pharmacodynamic activities of the individual enantiomers, therapeutic drug monitoring may be employed based on specific enantiomer target concentration ranges in plasma for the racemic preparation of perhexiline, or by developing a target concentration for a chiral preparation.

As indicated, the preferred subject for treatment is a human. However, the treatment may be a veterinary one. For example, treatment of cats suffering from feline HCM is contemplated.

The invention is illustrated by the following non-limiting examples.

EXAMPLE

A study was carried out to establish a causative role for energy deficiency and to evaluate the impact of perhexiline on cardiac energy status in HCM.

Figure 1:
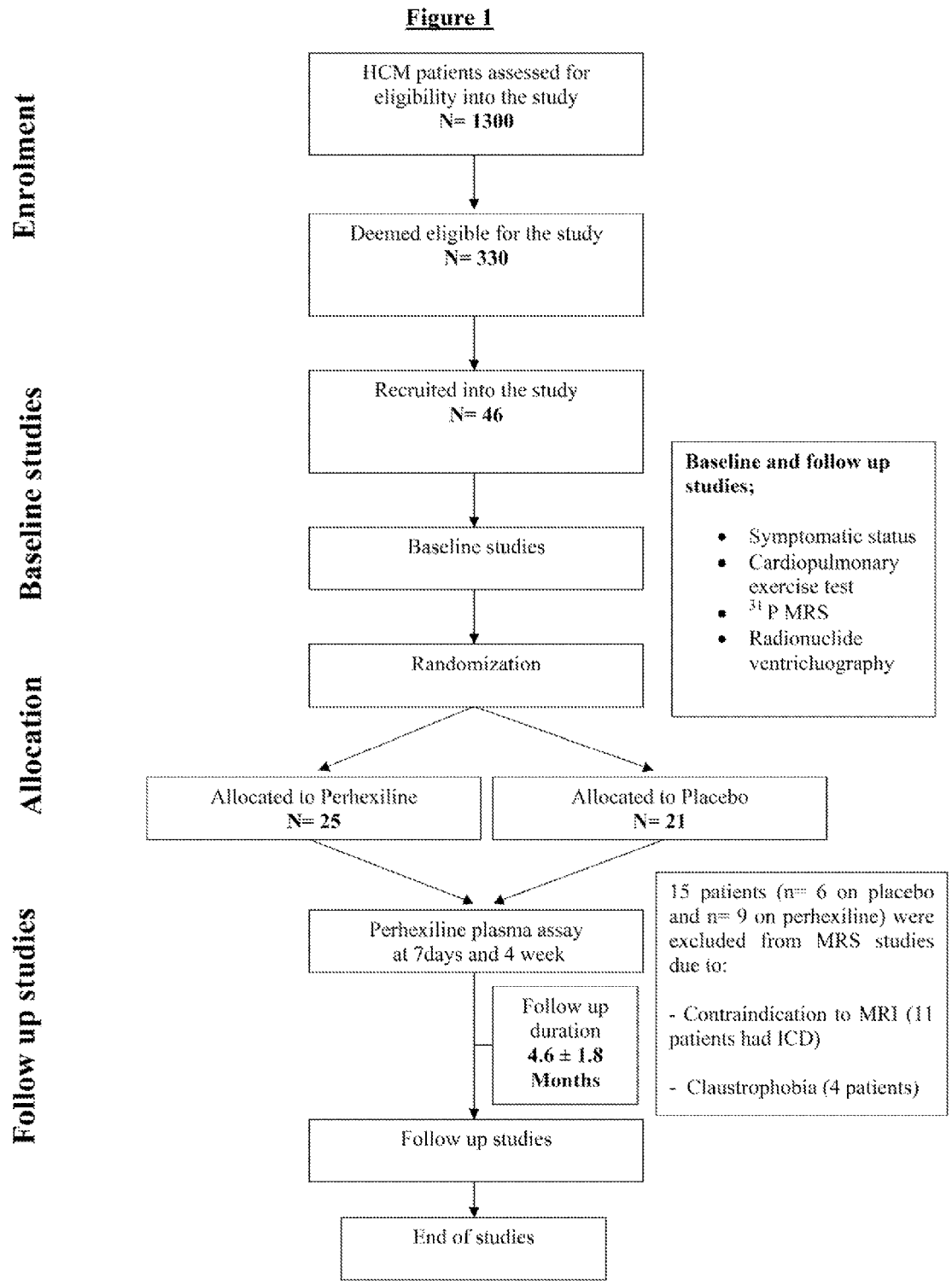
FIG. 1 is a flow chart of a study carried out to establish a causative role for energy deficiency and to evaluate the impact of perhexiline on cardiac energy status in HCM.

The study was approved by the South Birmingham Research Ethics Committee and the investigation conforms with the principles outlined in the Declaration of Helsinki. All study participants provided written informed consent. The study was a randomized, double blind, placebo-controlled parallel-group design of minimum 3 months duration. FIG. 1 represents a flow chart of the study. The pre-defined primary end point was peak oxygen consumption (peak VO2). Pre-defined secondary end points were symptomatic status, resting myocardial energetics (PCr/γ-ATP ratio) and diastolic function at rest and during exercise (nTTPF). 33 controls of similar age and gender distribution were recruited for comparison with baseline data of HCM patients. All controls had no history or symptoms of any cardiovascular disease with normal ECG and echocardiogram (LVEF≥55%).

Patients were recruited from dedicated cardiomyopathy clinics at The Heart Hospital, University College London Hospitals, London and Queen Elizabeth Hospital, Birmingham, UK between 2006 and 2008. Inclusion criteria were 18 to 80 years old symptomatic HCM patients (predominant symptom breathlessness) in sinus rhythm with reduced peak VO2 (<75% of predicted for age and gender) and no significant LVOT obstruction at rest (gradient<30 mmHg). Exclusion criteria were presence of epicardial coronary artery disease, abnormal liver function test, concomitant use of amiodarone or selective serotonin reuptake inhibitors (due to potential drug interactions with perhexiline), peripheral neuropathy and women of childbearing potential. Diabetic patients were also excluded to maintain the blindness of the study as Perhexiline may lead to a reduction in plasma glucose in such patients necessitating a reduction in anti-diabetic therapy. 46 consecutive consenting patients who met these entry criteria were recruited into the study.

Patients were subjected to a number of tests and assessments as follows.

Cardiopulmonary Exercise Test

This was performed using a Schiller CS-200 Ergo-Spiro exercise machine which was calibrated before every study. Subjects underwent spirometry and this was followed by symptom-limited erect treadmill exercise testing using a standard ramp protocol with simultaneous respiratory gas analysis (Bruce R A, McDonough J R. Stress testing in screening for cardiovascular disease. Bull N Y Acad Med 1969; 45(12): 1288-1305.; Davies N J, Denison D M. The measurement of metabolic gas exchange and minute volume by mass spectrometry alone. Respir Physiol 1979;36(2):261-267). Peak oxygen consumption (peak VO2) was defined as the highest VO2 achieved during exercise and was expressed in ml/min/kg.

Symptomatic Status Assessment

All HCM patients filled in Minnesota Living with heart failure questionnaire and were also assessed for NHYA class.

Transthoracic Echocardiography

Echocardiography was performed with participants in the left lateral decubitus position with a Vivid 7 echocardiographic machine (GE Healthcare) and a 2.5-MHz transducer. Resting scans were acquired in standard apical 4-chamber and apical 2-chamber. LV volumes were obtained by biplane echocardiography, and LVEF was derived from a modified Simpson's formula (Lang R M, Bierig M, Devereux R B et al. Recommendations for chamber quantification: a report from the American Society of Echocardiography's Guidelines and Standards Committee and the Chamber Quantification Writing Group, developed in conjunction with the European Association of Echocardiography, a branch of the European Society of Cardiology. J Am Soc Echocardiogr 2005;18(12): 1440-1463.) Pulse wave doppler sample volume was used to assess resting LVOTO gradient.

Radionuclide Ventriculography

Diastolic filling were assessed by equilibrium R-wave gated blood pool scintigraphy using a standard technique at rest and during graded semi erect exercise on a cycle ergometer (Atherton J J, Moore T D, Lele S S et al. Diastolic ventricular interaction in chronic heart failure. Lancet 1997; 349 (9067):1720-1724; Lele S S, Macfarlane D, Morrison S, Thomson H, Khafagi F, Frenneaux M. Determinants of exercise capacity in patients with coronary artery disease and mild to moderate systolic dysfunction. Role of heart rate and diastolic filling abnormalities. Eur Heart J 1996;17(2):204-212).

Peak left ventricular filling rate in terms of end-diastolic count per second (EDC/s) and time to peak filling normalised for R-R interval (nTTPF) in milliseconds were measured at rest and during exercise (50% of heart rate reserve). The validity of these radionuclide measures of diastolic filling at high heart rates has been established previously (Atherton et al. and Lele et al., see above).

31P Cardiac Magnetic Resonance Spectroscopy (MRS)

Figure 2:
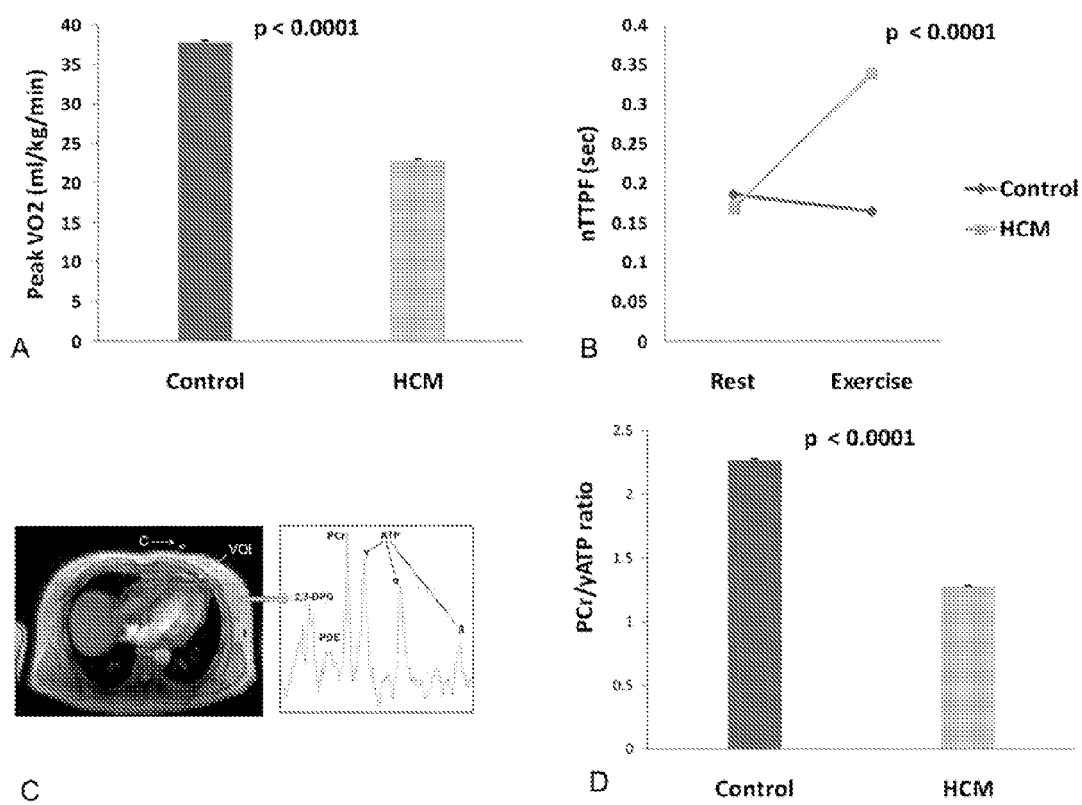
FIGS. 2A-2D represent the baseline data of HCM vs controls, more particularly.

In vivo myocardial energetics were measured using a MRS at 3-Tesla Phillips Achieva 3T scanner (Shivu G N, Abozguia K, Phan T T, Ahmed I, Henning A, Frenneaux M. (31)P magnetic resonance spectroscopy to measure in vivo cardiac energetics in normal myocardium and hypertrophic cardiomyopathy: Experiences at 3T. Eur J Radiol 2008). A java magnetic resonance user interface v3.0 (jMRUI) was used for analysis (see Naressi A, Couturier C, Castang I, de Beer R, Graveron-Demilly D. Java-based graphical user interface for MRUI, a software package for quantitation of in vivo/medical magnetic resonance spectroscopy signals. Comput Biol Med 2001;31(4):269-286)). PCr and γ-ATP peaks was used to determine the PCr/γ-ATP ratio which is a measure of the cardiac energetic state (Neubauer S, Krahe T, Schindler R et al. 31P magnetic resonance spectroscopy in dilated cardiomyopathy and coronary artery disease. Altered cardiac high-energy phosphate metabolism in heart failure. Circulation 1992;86(6):1810-1818). Data were analyzed by an investigator who was blinded to the participants' clinical status. Carmeo-Rao ratio was used to assess signal to noise ratio. A typical example of cardiac 31 P MRS spectra from a patient with HCM is shown in FIG. 2C.

Intervention

Following baseline studies, patients were randomized in a double-blind fashion to receive either perhexiline (n=25) or placebo (n=21) 100 mg OD. Serum perhexiline levels were obtained at 1 and 4 weeks after initiation of the drug. Dose adjustments were advised by an unblinded physician according to serum level to achieve therapeutic level and to avoid drug toxicity. Identical dosage adjustments were also made for randomly allocated placebo-treated patients by the unblinded observer to ensure that blinding of the investigators was maintained. At the end of study, patients were re-evaluated as described earlier.

Statistical Analysis

Data were analyzed using SPSS ver. 15.0 for Window and Microsoft Office Excel 2007, and expressed as Mean±Standard Deviation (SD). Comparison of continuous variables between Perhexiline and Placebo baseline data were determined by unpaired Student's t-test (2-tail) if variables were normally distributed and the Mann-Whitney U-test if the data were non-normally distributed. ANCOVA with baseline values as covariates was performed to test for the significance of differences in the perhexiline versus placebo group after treatment. For the primary end point, the sample size required to detect a change in peak Vo2 of 3 ml/kg/min versus placebo group with a power of 90% and probability of 5% is 44. 30 patients will be required to identify a 5% change in cardiac PCr/ATP ratio with a power of 90% and a p value of <0.05. 40 patients will be required to detect a change ≥25% in nTTPF with power of 0.99 with probability of 5%. Therefore, we aimed to study 50 patients including the drop-outs, 32 of them will take part in the MRS study.

The characteristics and treatment of participants are shown in Table 1 below. $Vo_2$: refers to peak oxygen consumption, ACE: refers to angiotensin-converting enzyme, and ARB refers to angiotensin II receptor blockers.

TABLE 1

The clinical characteristics of HCM patients and controls.

|  | HCM | Controls | P value | HCM (Perhexiline) | HCM (Placebo) | P value |
|---|---|---|---|---|---|---|
| Age [years] | 55 ± 0.26 | 52 ± 0.46 | 0.2 | 56 ± 0.46 | 54 ± 0.64 | 0.42 |
| Number (Male) | 46 (34) | 33 (20) | 0.64 | 25 (19) | 21 (17) | 0.69 |
| Heart Rate [bpm] | 69 ± 0.27 | 82 ± 0.47 | <0.001* | 69 ± 0.53 | 69 ± 0.52 | 0.97 |
| Systolic BP [mmHg] | 126 ± 0.64 | 126 ± 0.44 | 0.93 | 123 ± 0.84 | 130 ± 0.92 | 0.2 |
| Diastolic BP [mmHg] | 76 ± 0.25 | 78 ± 0.34 | 0.33 | 74 ± 0.45 | 78 ± 0.57 | 0.24 |
| Peak $Vo_2$ [ml/kg/min] | 23 ± 0.12 | 38 ± 0.24 | <0.0001* | 22.2 ± 0.2 | 23.56 ± 0.27 | 0.42 |
| Resting nTTPF (sec) | 0.17 ± 0.002 | 0.18 ± 0.003 | 0.44 | 0.19 ± 0.003 | 0.17 ± 0.004 | 0.52 |
| PCr/γATP ratio | 1.28 ± 0.01 | 2.26 ± 0.02 | <0.0001* | 1.27 ± 0.02 | 1.29 ± 0.01 | 0.86 |
| Drug therapy - no. |  |  |  |  |  |  |
| Beta-blocker | 17 | 0 | — | 10 | 7 | 0.21 |
| CC-blocker | 24 | 0 | — | 11 | 8 | 0.53 |
| Diuretic | 10 | 0 | — | 4 | 5 | 0.49 |
| ACE inhibitor | 6 | 0 | — | 3 | 2 | 0.84 |
| ARB | 4 | 0 | — | 3 | 1 | 0.41 |
| Warfarin | 5 | 0 | — | 2 | 3 | 0.48 |
| Statin | 15 | 0 | — | 7 | 7 | 0.9 |

*indicates statistical significance

Baseline Data (HCM Versus Controls)

The clinical characteristics and cardiopulmonary exercise test results of all the HCM patients and controls are shown in Table 1. The groups were well matched with respect to age and gender. Heart rate was lower in the HCM group compared to controls due to medication use (beta blockers and/or calcium channel blockers).

The resting cardiac PCr/γATP ratio was lower in HCM patients than in controls (1.28±0.01 vs 2.26±0.02, p<0.0001) (see FIGS. 2A and B), and this remained so after excluding patients taking beta blocker therapy (p<0.0001). At rest, nTTPF, a sensitive marker of LV relaxation, was similar in HCM patients and controls (0.17±0.002 vs 0.18±0.003 sec, p=0.44). During submaximal exercise (at a workload that achieved 50% of heart rate reserve) it remained relatively constant in controls (from 0.18±0.003 sec to 0.16±0.002 sec, [δnTTPF=−0.02±0.003 sec]), but lengthened in patients (from 0.17±0.002 to 0.34±0.002 sec, [εnTTPF=+0.17±0.002 sec]) p<0.0001, (FIG. 2C). This pattern persisted after exclusion of patients on beta blockers and remained significantly different from controls (p<0.0001). Patients exhibited marked exercise limitation compared to controls (23±0.12 vs 38±0.24 ml/kg/min, p<0.0001) (FIG. 2D).

Randomized, Double Blinded, Placebo-controlled Parallel-group

The perhexiline and placebo groups were well matched (see Table 1). Only one patient (on placebo) did not complete the study due to poor compliance. Side effects were restricted to transient nausea (n=3) and dizziness (n=2) in the perhexiline group and transient nausea (n=2) and headache (n=1) in the placebo group during the first week of treatment. There were no deaths during the study period.

Myocardial Energetics

Figure 3:
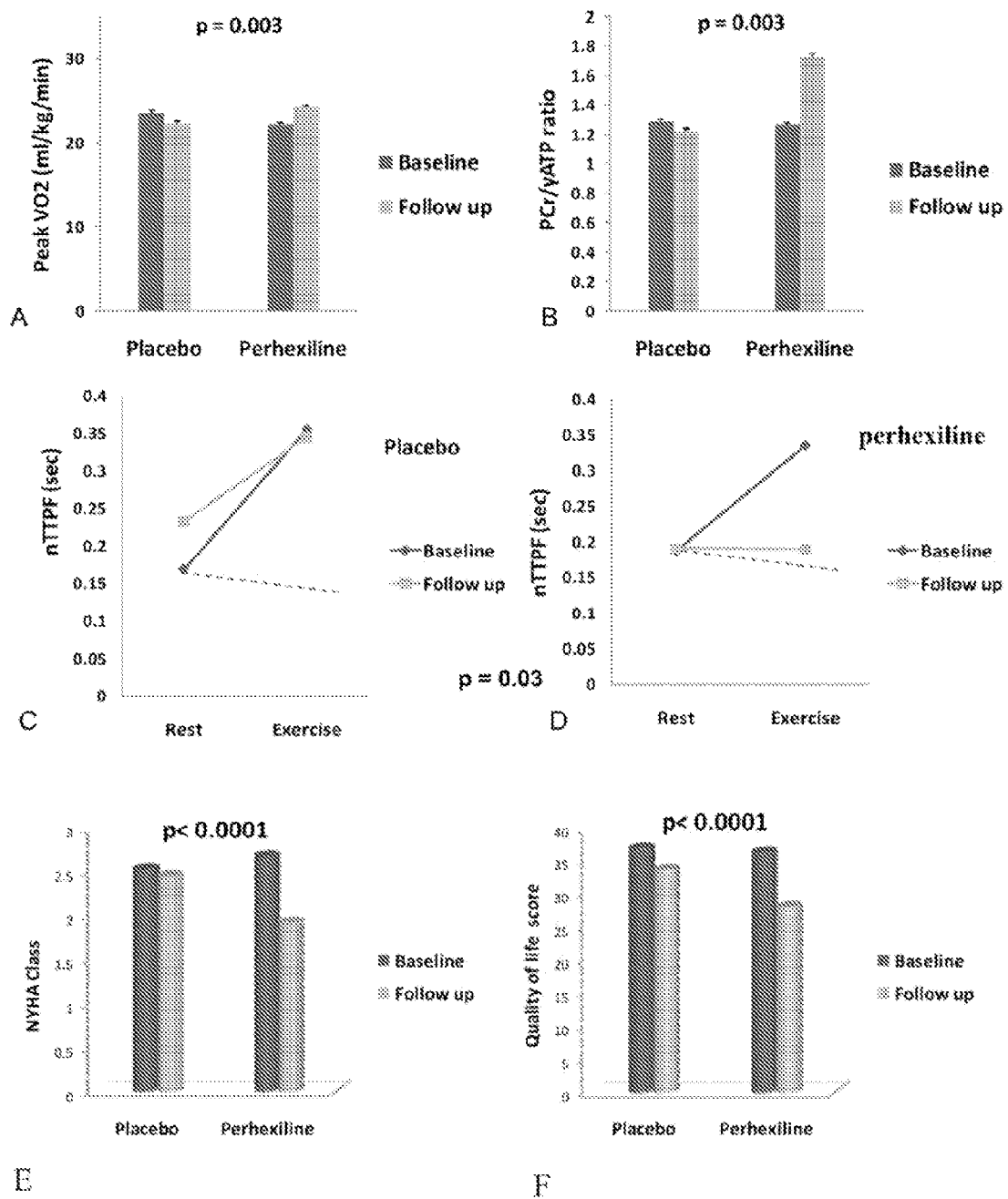
FIGS. 3A and 3B respectively represent the effect of Placebo and Perhexiline on peak oxygen consumption (peak $V_{O2}$), p=0.003 and myocardial energetic (PCr/γATP ratio), p=0.003, where the p value represents the significant difference between perhexiline and placebo response. Peak VO2 (exercise capacity) increases with Perhexiline (FIG. 3A). Perhexiline improves PCr/ATP ratio (energetic status of heart), but this was unchanged in the placebo group (FIG. 3B).
FIGS. 3C and 3D respectively represent nTTPF changes in the placebo group (3C) and the perhexiline group (3D), p=0.03, where the p value represents the significant difference between perhexiline and placebo response. In the placebo group nTTPF (a measure of the rate of LV active relaxation) abnormally lengthened at baseline and on treatment. The response in healthy controls is shown in dotted lines. Perhexiline (FIG. 3D) normalises the response to similar to that seen in healthy controls (also shown in dotted lines).
FIG. 3E and 3F illustrate that NYHA score (of breathlessness) falls (improves) with perhexiline (3E) and Minnesota living with heart failure questionnaire score falls (=improved quality of life) on perhexiline (3F).

The PCr/γATP ratio increased with perhexiline (1.27±0.02 to 1.73±0.02) as compared with placebo (1.29±0.01 to 1.23±0.01), p=0.003 (see FIG. 3A). The mean Cramer-Rao ratios for PCr and γATP were 7.5% and 10.8% respectively. The effect of perhexiline on PCr/γATP ratio remained significant after inclusion of the 3 patients with Cramer Rao ratios >20 from the analysis (p=0.02).

Diastolic Ventricular Filling

Whereas the placebo group showed similar prolongation of nTTPF during exercise before and after therapy (0.17±0.004 to 0.35±0.005 [∈nTTPF 0.18±0.006 sec] and 0.23±0.006 to 0.35±0.005 sec [∈nTTPF 0.12±0.006 sec], respectively), in the perhexiline group there was a substantial improvement on therapy with nTTPF at rest and exercise similar (0.19±0.003 to 0.19±0.004 sec[∈nTTPF 0.00±0.003 sec]) p=0.03 between the perhexiline and placebo response (see FIGS. 3B and 3C).

Symptomatic Status

More patients in the perhexiline group than in the placebo group had improvements in NYHA classification (67 percent vs. 30 percent) and fewer had worsening (8 percent vs. 20 percent) (p<0.001). Minnesota Living with heart failure questionnaire score showed an improvement (fall in score) in the perhexiline group (from 36.13±0.94 to 28±0.75) but did not change in the placebo group (p<0.001) (see FIGS. 3D and 3E).

Exercise Capacity (Peak Oxygen Consumption)

Peak $V_{O2}$ at baseline was similar in the perhexiline and placebo groups (Table 1). After treatment, Peak $V_{O2}$ fell by −1.23 ml/kg/min in the placebo group (from 23.56±0.27 to 22.32±0.27 ml/kg/min) but increased by 2.09 ml/kg/min in the perhexiline group (from 22.2±0.2 to 24.29±0.2 ml/kg/min), p=0.003 (see FIG. 3F).

Discussion of Results

Figure 4:
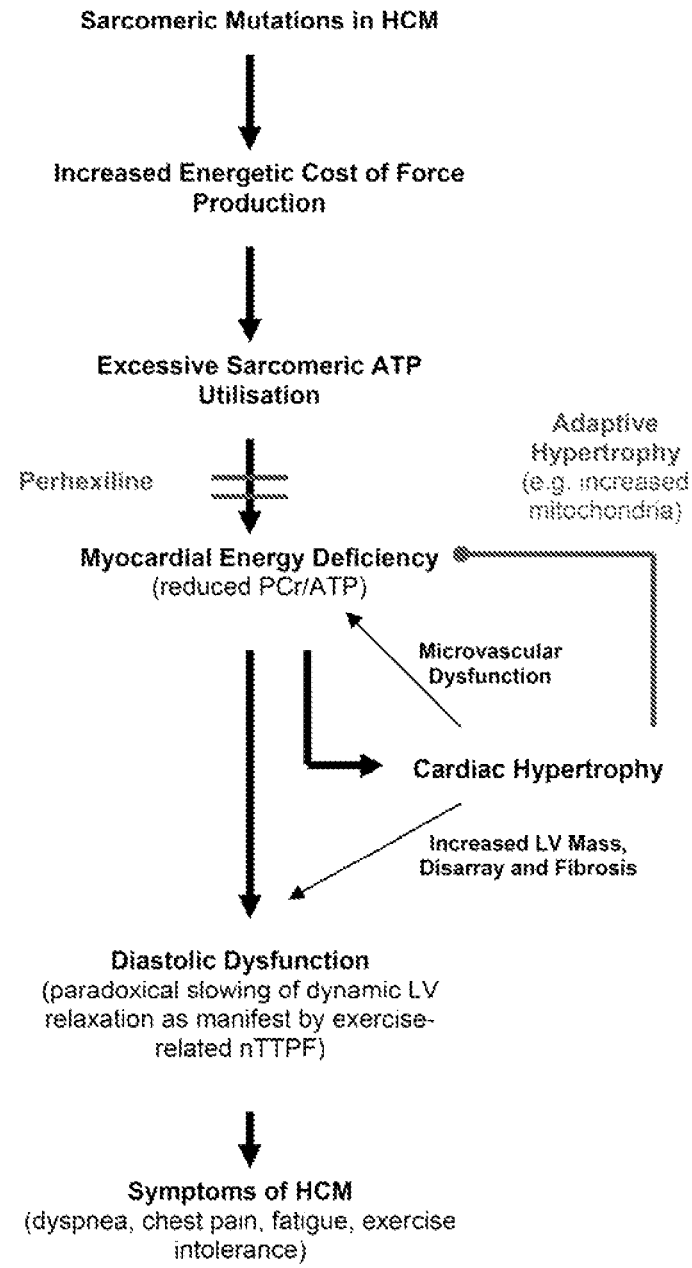
FIG. 4 illustrate the causative role for energy deficiency in the pathophysiology of HCM.

The study indicates that patients with symptomatic HCM manifest a cardiac energy defect at rest (reduced PCr/γATP ratio). This defect was accompanied by a slowing of the energy-requiring early diastolic LV active relaxation during exercise (prolongation of nTTPF). The metabolic modulator perhexiline resulted in significant myocardial energy augmentation. Supporting a causative role for energy deficiency in the pathophysiology of HCM, this energy augmentation was accompanied by striking normalisation of HCM's characteristic "paradoxical" nTTPF-prolongation in exercise. These biochemical and physiological improvements translated into significant subjective (NYHA classification and QoL score) and objective ($V_{O2}$) clinical benefits in symptomatic HCM patients already on optimal medical therapy (see FIG. 4).

The invention claimed is:

1. A method for treating hypertrophic cardiomyopathy consisting of diastolic dysfunction, or a symptomatic component/feature/condition thereof, in a mammal, comprising: diagnosing the mammal as having hypertrophic cardiomyopathy consisting of diastolic dysfunction, or a symptomatic component/feature/condition thereof; and administering to said mammal a therapeutically-effective amount of perhexiline.

2. The method of claim 1, wherein the therapeutically-effective amount of perhexiline is sufficient to reduce or ameliorate the hypertrophic cardiomyopathy or a symptomatic component/feature/condition thereof in the mammal.

3. The method of claim 2, wherein the perhexiline is in the form of a maleate salt.

4. The method of claim 1, wherein the perhexiline is in the form of a pharmaceutically acceptable salt.

5. The method of claim 1, wherein the mammal is a human.

6. The method of claim 1, further comprising co-administering to said mammal at least one therapeutic compound.

7. The method of claim 6, wherein the therapeutic compound is selected from a member of the group consisting of Alpha Blockers, Beta Blockers, Calcium Channel Blockers, Diuretics, Ace (Angiotensin-Converting Enzyme) Inhibitors, Arb (Angiotensin II Receptor Blockers), Spironolactone, Nitrate, Warfarin, Verapamil, Insulin, Amiodarone, Lisinopril, Ramipril, Perindopril, Enalapril, Trandolapril, At2 Receptor Blockers, Losartan, Valsartan, Irbersartan, Carvedilol, Bisoprolol, Metoprolol, Atenolol, Aspirin, Clopidogrel, Oral Hypoglycaemics, Disopyramide, and Statins.

8. The method of claim 1, further comprising co-administering to said mammal at least one therapeutic compound advantageous in treating hypertrophic cardiomyopathy or a symptomatic component/feature/condition thereof.

9. The method of claim 1, wherein the symptomatic component/feature/condition is selected from a member of the group consisting of dyspnoea (shortness of breath), chest pain, fatigue, palpitation and syncope.

10. The method of claim 9, further comprising:
    determining a NYHA classification score (breathlessness) of the mammal before and after administration of perhexline, wherein a decreased NYHA score after administration of perhexline indicates a reduction in the extent of hypertrophic cardiomyopathy or a symptomatic component/feature/condition thereof in the mammal.

11. The method of claim 10, wherein the NYHA classification score of the mammal after administration of perhexline decreases from Class III to Class II.

12. The method of claim 1, wherein the symptomatic component/feature/condition is selected from a member of the group consisting of, reduced E:EA ratio, abnormally rapid skeletal muscle phosphocreatine depletion with delayed recovery, reduced systolic velocity (PSV), diminished exercise capacity or tolerance, diminished peak oxygen consumption ($VO_2max$) during exercise, diastolic dysfunction at rest and during exercise as measured by Time to Peak LV Filling (nTTPF), and impaired myocardial energetic state (PCr/γATP ratio).

13. The method of claim 1, wherein the extent of hypertrophic cardiomyopathy in the mammal is assessed in accordance with the New York Heart Association (NYHA).

14. The method of claim 1, wherein the extent of hypertrophic cardiomyopathy in the mammal is assessed in accordance with the Minnesota Living with Heart Failure Questionnaire (MLHFQ) scoring system.

15. The method of claim 14, further comprising
    determining a MLHFQ (quality of life) score of the mammal before and after administration of perhexline, wherein a decreased MLHFQ score after administration of perhexline indicates a reduction in the extent of hypertrophic cardiomyopathy or a symptomatic component/feature/condition thereof in the mammal.

16. The method of claim 1, wherein perhexiline is administered in an amount of 300 mg per day or less.

17. The method of claim 1, wherein perhexiline is administered in an amount of 100 mg per day or less.

18. The method of claim 1, wherein perhexiline is administered in an amount of 100 mg to 300 mg per day.

* * * * *